United States Patent [19]

Slaugh et al.

[11] Patent Number: 5,723,389
[45] Date of Patent: Mar. 3, 1998

[54] PROCESS FOR PREPARING ALKANEDIOLS

[75] Inventors: Lynn Henry Slaugh; Paul Richard Weider; Joseph Broun Powell, all of Houston; Juan Pedro Arhancet, Katy, all of Tex.

[73] Assignee: Shell Oil Company, Houston, Tex.

[21] Appl. No.: 729,932

[22] Filed: Oct. 15, 1996

[51] Int. Cl.⁶ .................. C07C 47/02; C07C 27/04; C07C 27/00; C07C 45/00
[52] U.S. Cl. .................. 468/862; 568/496; 568/867; 568/483
[58] Field of Search .................. 568/496, 862, 568/867, 483

[56] References Cited

U.S. PATENT DOCUMENTS

| | | | |
|---|---|---|---|
| 3,168,553 | 2/1965 | Slaugh | 260/497 |
| 3,687,981 | 8/1972 | Lawrence | 260/340.7 |
| 4,973,741 | 11/1990 | Beavers | 560/179 |
| 5,210,318 | 5/1993 | Briggs | 568/496 |
| 5,256,827 | 10/1993 | Slaugh | 568/454 |
| 5,563,144 | 10/1996 | Powell | 568/867 |

*Primary Examiner*—Gary Geist
*Assistant Examiner*—Karl J. Puttlitz, Jr.

[57] ABSTRACT

An alkanediol such as 1,3-propanediol is prepared in a process which involves reacting an alkylene oxide with carbon monoxide and hydrogen in an essentially non-water-miscible solvent in the presence of a non-phosphine-ligated cobalt or rhodium catalyst and a cobalt or rhodium porphyrin promoter to produce an intermediate product mixture containing a hydroxyalkanal in an amount less than 15 wt %; extracting the hydroxyalkanal from the intermediate product mixture into an aqueous liquid at a temperature less than about 100° C. and separating the aqueous phase containing hydroxyalkanal from the organic phase containing cobalt catalyst; hydrogenating the hydroxyalkanal in the aqueous phase to an alkanediol; and recovering the alkanediol.

The process enables the production of an alkanediol such as 1,3-propanediol in high yields and selectivity without the use of a phosphine ligand with the cobalt or rhodium catalyst.

19 Claims, 1 Drawing Sheet

PROCESS FOR PREPARING ALKANEDIOLS

BACKGROUND OF THE INVENTION

This invention relates to the preparation of alkanediols including 1,3-propanediol. In a specific aspect, the invention relates to a cobalt-catalyzed process for manufacturing 1,3-propanediol in high yields without the use of a phosphine ligand for the cobalt catalyst.

1,3-propanediol (PDO) is an intermediate in the production of polyesters for fibers and films. It is known to prepare PDO in a two-step process involving (1) the cobalt-catalyzed hydroformylation (reaction with synthesis gas, $H_2/CO$) of ethylene oxide to intermediate 3-hydroxypropanal (HPA) and (2) hydrogenation of the HPA to PDO. The initial hydroformylation step can be carried out at temperatures greater than 100° C. and at high syngas pressures to achieve practical reaction rates. The resulting product mixture is, however, rather unselective for HPA.

In an alternate hydroformylation method, the cobalt catalyst is used in combination with a phosphine ligand to prepare HPA with greater selectivity and at lower temperature and pressure. However, the use of a phosphine ligand adds to the cost of the catalyst and increases the complexity of catalyst recycle.

It would be desirable to prepare PDO and other alkanediols in a low temperature, selective process which permitted efficient recycle of the catalyst.

It is therefore an object of the invention to provide a process for the preparation of alkanediols. In a specific embodiment, it is an object of the invention to provide an economical process for the preparation of 1,3-propanediol which does not require the use of a phosphine-ligated catalyst for preparation of the HPA intermediate.

SUMMARY OF THE INVENTION

According to the invention, an alkanediol is prepared in a process comprising the steps of:

(a) contacting an alkylene oxide with carbon monoxide and hydrogen in an essentially non-water-miscible solvent in the presence of an effective amount of a non-phosphine-ligated cobalt or rhodium catalyst and an effective amount of a cobalt or rhodium porphyrin promoter at a temperature within the range of about 50 to about 100° C. and a pressure within the range of about 500 to about 5000 psig, under reaction conditions effective to produce an intermediate product mixture comprising less than 15 wt % hydroxyaldehyde;

(b) adding an aqueous liquid to said intermediate product mixture and extracting into said aqueous liquid at a temperature less than about 100° C. a major portion of the hydroxyaldehyde to provide an aqueous phase comprising hydroxyaldehyde in greater concentration than the concentration of hydroxyaldehyde in said intermediate product mixture, and an organic phase comprising at least a portion of the cobalt or rhodium catalyst and at least a portion of the porphyrin promoter;

(c) separating the aqueous phase from the organic phase;

(d) contacting the aqueous phase comprising hydroxyaldehyde with hydrogen in the presence of a hydrogenation catalyst at a pressure of at least about 100 psig and a temperature during at least a portion of the hydrogenation step of at least 40° C. to provide a hydrogenation product mixture comprising an alkanediol; and (e) recovering the alkanediol from said hydrogenation product mixture.

The process enables the production of alkanediols such as 1,3-propanediol in high yields and selectivity without the use of a phosphine-ligated catalyst in the hydroformylation step.

DETAILED DESCRIPTION OF THE INVENTION

Figure 1:
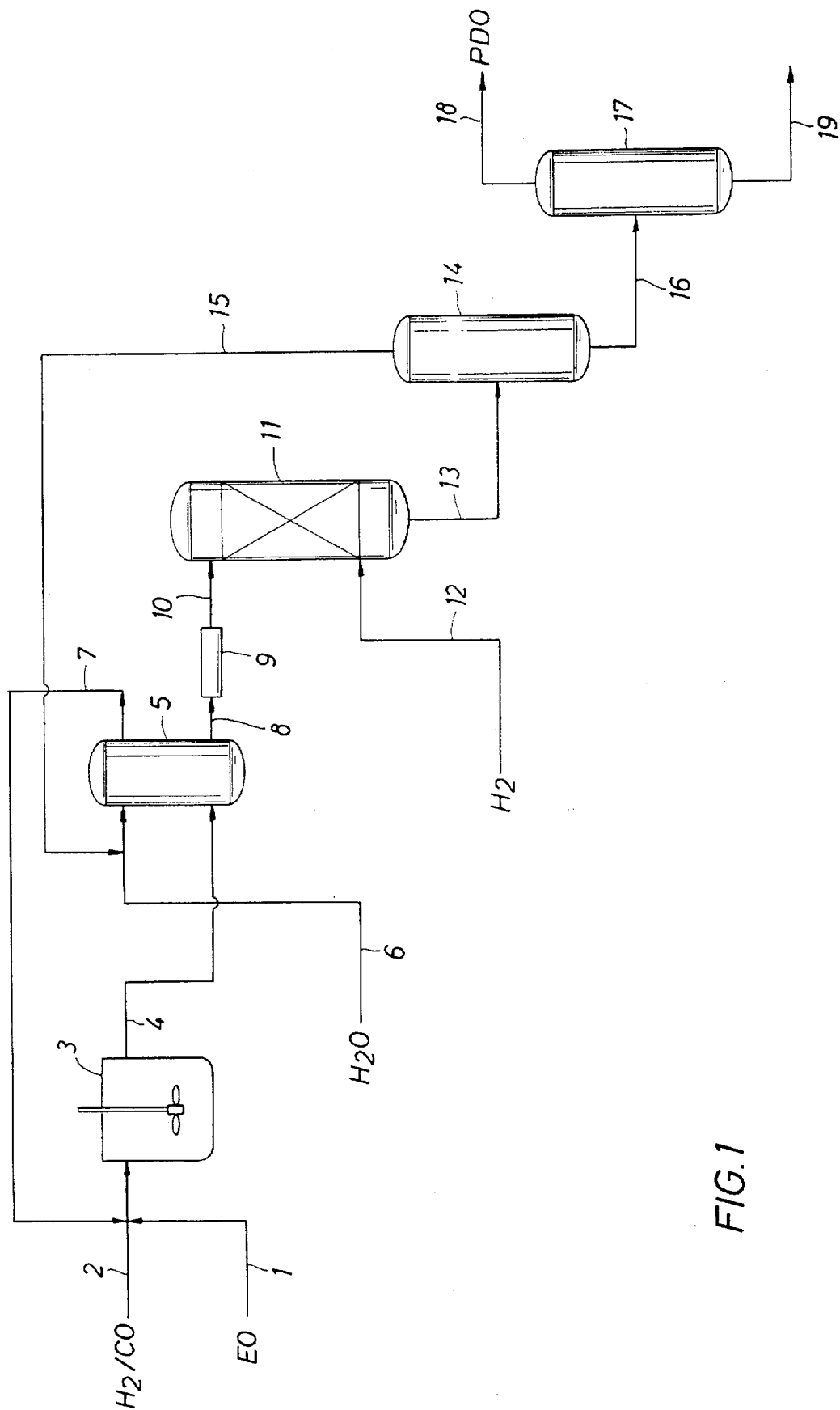
FIG. 1 is a schematic flow diagram of one embodiment of the invention alkanediol preparation process.

In the invention process, an alkylene oxide is reacted with carbon monoxide and hydrogen to produce an intermediate hydroxyaldehyde, which is then hydrogenated to the desired alkanediol. Suitable alkylene oxide starting materials can be described by the formula $RCHOCH_2$, in which R is hydrogen (ethylene oxide) or $C_{1-3}$ alkyl (propylene oxide, butylene oxide, pentylene oxide). The intermediate hydroxyaldehyde can be represented by the formula

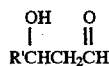

in which R' is hydrogen or $C_{1-3}$ alkyl including, for example, hydroxyaldehydes such as 3-hydroxypropanal, 3-hydroxybutanal, 3-hydroxypentanal, and 3-hydroxyhexanal.

Correspondingly, the alkanediol can be represented by the formula

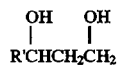

where R' is as described above. Such alkanediols include 1,3-propanediol, 1,3-butanediol, 1,3-pentanediol and 1,3-hexanediol. For simplicity, the process will be described, by reference to FIG. 1, in terms of starting with ethylene oxide to produce 1,3-propanediol.

In FIG. 1, separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a non-phosphine-ligated cobalt or rhodium catalyst, i.e., a cobalt carbonyl or rhodium carbonyl composition which has not been prereacted with a phosphine ligand, and the porphyrin promoter. The hydrogen and carbon monoxide will generally be introduced into the reaction vessel in a molar ratio within the range of about 1:2 to about 8:1, preferably about 1:1 to about 6:1.

The reaction is carried out under conditions effective to produce a hydroformylation reaction product mixture containing a major portion of 3-hydroxypropanal (HPA) and a minor portion of acetaldehyde and diol, while maintaining the level of 3-hydroxypropanal in the reaction mixture at less than 15 wt %, preferably within the range of about 5 to about 10 wt %. (To provide for solvents having different densities, the desired concentration of HPA in the reaction mixture can be expressed in molarity, i.e., less than 1.5M, preferably within the range of about 0.5 to about 1M.) Generally, the hydroformylation reaction is carried out at elevated temperature less than 100° C., preferably about 60 to about 90° C., most preferably about 70 to about 85° C. and at a pressure within the range of about 500 to about 5000 psig, preferably (for process economics) about 1000 to about 3500 psig, with higher pressures preferred for greater selectivity. The concentration of 3-hydroxypropanal in the intermediate product mixture can be controlled by regulation of process conditions such as ethylene oxide concentration, catalyst concentration, reaction temperature and residence time. In the practice of the invention method, it is possible to achieve HPA yields (based on ethylene oxide conversion) of greater than 70%, with formation of greater than 7 wt % HPA, at rates greater than 30 $h^{-1}$. (Catalytic rates are referred to herein in terms of "turnover frequency" or "TOF" and are expressed in units of moles per mole of metal per hour, or $h^{-1}$.)

The hydroformylation reaction is carried out in a liquid solvent inert to the reactants. By "inert" is meant that the solvent is not consumed during the course of the reaction. In general, ideal solvents for the phosphine ligand-free process will solubilize carbon monoxide, will be essentially non-water-miscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt %, so as to form a separate hydrocarbon-rich phase upon water extraction of HPA from the hydroformylation reaction mixture. Preferably this solubility is less than about 10%, most preferably less than about 5 wt %. The solubilization of carbon monoxide in the selected solvent will generally be greater than 0.15 v/v (1 atm, 25° C.), preferably greater than 0.25 v/v, as expressed in terms of Ostwald coefficients.

The preferred class of solvents are alcohols and ethers which can be described according to the formula

 (1)

in which $R_1$ is hydrogen or $C_{1-20}$ linear, branched, cyclic or aromatic hydrocarbyl or mono- or polyalkylene oxide and $R_2$ is $C_{1-20}$ linear, branched, cyclic or aromatic hydrocarbyl, alkoxy or mono- or polyalkylene oxide. The most preferred hydroformylation solvents can be described by the formula

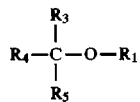 (2)

in which $R_1$ is hydrogen or $C_{1-8}$ hydrocarbyl and $R_3$, $R_4$ and $R_5$ are independently selected from $C_{1-8}$ hydrocarbyl, alkoxy and alkylene oxide. Such ethers include, for example, methyl-t-butyl ether, ethyl-t-butyl ether, diethyl ether, phenylisobutyl ether, ethoxyethyl ether, diphenyl ether and diisopropyl ether. Blends of solvents such as tetrahydrofuran/toluene, tetrahydrofuran/heptane and t-butylalcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated cobalt or rhodium carbonyl compound. Although phosphine-ligated catalysts are active for hydroformylation reactions, the invention process is designed to achieve good yield and selectivity without the additional expense of the ligand. The catalyst can be supplied to the hydroformylation reactor in essentially any form including metal, supported metal, hydroxide, oxide, carbonate, sulfate, acetylacetonate, salt of a carboxylic acid, or as an aqueous salt solution, for example. It may be supplied directly as a cobalt or rhodium carbonyl such as dicobaltoctacarbonyl or cobalt hydridocarbonyl (tetrarhodium dodecacarbonyl or dicarbonylacetylacetonato rhodium), or operating conditions can be adjusted such that carbonyls are formed in situ via reaction with $H_2$ and CO, as described in J. Falbe, "Carbon Monoxide in Organic Synthesis," Springer-Verlag, N.Y. (1970). In general, catalyst formation conditions will include a temperature of at least 50° C. and a carbon monoxide partial pressure of at least about 100 psig. For more rapid reaction, temperatures of about 120° to 200° C. should be employed, at CO pressures of at least 500 psig. Addition of high surface area activated carbons or zeolites, especially those containing or supporting platinum or palladium metal, can accelerate cobalt carbonyl formation from noncarbonyl precursors. The resulting catalyst is maintained under a stabilizing atmosphere of carbon monoxide, which also provides protection against exposure to oxygen. The most economical and preferred cobalt catalyst activation and reactivation (of recycled catalyst) method involves preforming the cobalt carbonyl under $H_2$/CO from cobalt hydroxide in the presence of a small amount of seed cobalt carbonyl. The conversion of $Co^{2+}$ to the desired cobalt carbonyl is carried out at a temperature within the range of about 75° to about 200° C., preferably about 100° to about 140° C. and a pressure within the range of about 1000 to about 5000 psig for a time preferably less than about 3 hours. The preforming step can be carried out in a pressurized preforming reactor or in situ in the hydroformylation reactor.

The hydroformylation reaction mixture will preferably include a cobalt or rhodium porphyrin promoter to accelerate the reaction rate. Such promoters include substituted and unsubstituted porphines according to the formula

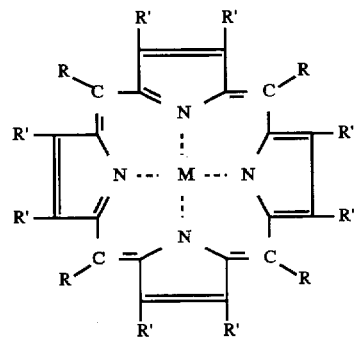

in which M is cobalt or rhodium and each of R and R' is selected independently from hydrogen, halide, alkoxy, aryloxy and substituted or unsubstituted hydrocarbyl including alkyl and aryl groups. The preferred such porphine, because of its commercial availability and demonstrated effectiveness, is 5, 10, 15, 20-tetraphenyl-21H,23H-porphine cobalt(II) CAS#[14172-90-8]. The cobalt or rhodium will generally be present in the promoter in an amount within the range of about 0.001 to about 0.5 mole per mole of cobalt metal in the hydroformylation catalyst, preferably about 0.008 to about 0.1 mole. Larger amounts of the porphyrin promoter can be used but are not necessary for promotional effect.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally being more tolerant of higher water concentrations. For example, optimum water levels for hydroformylation in methyl-t-butyl ether solvent are believed to be within the range of about 1 to about 2.5 wt %.

Following the hydroformylation reaction, hydroformylation reaction product mixture 4 containing 3-hydroxypropanal, the reaction solvent, 1,3-propanediol, the cobalt or rhodium catalyst (referred to in terms of cobalt catalyst hereinafter) and porphyrin promoter and a minor amount of reaction by-products, is cooled and passed to extraction vessel 5, wherein an aqueous liquid, generally water and optional miscibilizing solvent, are added via 6 for extraction and concentration of the HPA for the subsequent hydrogenation step. Liquid extraction can be effected by any suitable means, such as mixer-settlers, packed or trayed extraction columns, or rotating disk contactors. Extraction can, if desired, be carried out in multiple stages. The water-containing hydroformylation reaction product mixture can optionally be passed to a settling tank (not shown) for resolution of the mixture into aqueous and organic phases. The amount of water added to the hydroformylation reaction product mixture will generally be such as to provide a water:mixture ratio within the range of about 1:1 to about 1:20, preferably about 1:5 to about 1:15. The addition of water at this stage of the reaction may have the additional advantage of suppressing formation of undesirable heavy ends. Extraction with a relatively small amount of water provides an aqueous phase which is greater than 20 wt % HPA, preferably greater than 35 wt % HPA, permitting economical hydrogenation of the HPA to PDO and recovery of PDO product. The water extraction is preferably carried out at a temperature within the range of about 25° to about 55° C., with higher temperatures avoided to minimize condensation products (heavy ends) and catalyst conversion to inactive, water-soluble species. In order to maximize catalyst recovery, it is optional but preferred to perform the water extraction under 50 to 200 psig carbon monoxide at 25° to 55° C. Additional water extraction(s) may be desirable, particularly for higher molecular weight hydroxyaldehydes, to remove essentially all of the intermediate from the solvent phase.

The organic phase containing the reaction solvent and the major portion of the cobalt catalyst and porphyrin promoter can be recycled from the extraction vessel to the hydroformylation reaction via 7. Aqueous extract 8 is optionally passed through one or more acid ion exchange resin beds 9 for removal of any cobalt catalyst present, and the demetallized aqueous product mixture 10 is passed to hydrogenation vessel 11 and reacted with hydrogen 12 in the presence of a hydrogenation catalyst to produce a hydrogenation product mixture 13 containing 1,3-propanediol. The hydrogenation step may also revert some heavy ends to PDO. The solvent and extractant water 15 can be recovered by distillation in column 14 and recycled to the water extraction process via a further distillation (not shown) for separation and purge of light ends. PDO-containing product stream 16 can be passed to distillation column 17 for recovery of PDO 18 from heavy ends 19.

Hydrogenation of the HPA to PDO can be carried out in aqueous solution at an elevated temperature during at least a portion of the hydrogenation step of at least about 40° C., generally within the range of about 50° to about 175° C., under a hydrogen pressure of at least about 100 psig, generally within the range of about 200 to about 2000 psig. The reaction is carried out in the presence of a hydrogenation catalyst such as any of those based upon Group VIII metals, including nickel, cobalt, ruthenium, platinum and palladium, as well as copper, zinc and chromium and mixtures and alloys thereof. Fixed-bed nickel catalysts are currently preferred.

Commercial operation will require efficient catalyst recovery with essentially complete recycle of cobalt and porphyrin to the hydroformylation reaction. The preferred catalyst recovery process involves two steps, beginning with the above-described water extraction of HPA from the hydroformylation product mixture. A portion of the cobalt catalyst may remain in the organic phase, with the remaining cobalt passing into the water phase. The organic phase can be recycled to the hydroformylation reactor, with optional purge of heavy ends. Optionally, further demetallizing of catalyst in the water layer can be effected by any suitable method, such as complete or partial oxidation of cobalt followed by precipitation and filtration, distillation, deposition on a solid support, or extraction using a suitable extractant, preferably prior to final removal by ion exchange (9).

EXAMPLE 1

This example illustrates the hydroformylation of ethylene oxide using a cobalt porphyrin-promoted cobalt catalyst. 5,10,15,20-Tetraphenyl-21H,23H-porphine cobalt(II) (cobalt TPP) and dicobalt octacarbonyl were used as the source of the metals. The amount of each catalyst component is listed as mmoles of metal atoms to allow a quantitative comparison on an atomic basis. Reaction times were 1 hour.

To a 100-ml Parr autoclave containing 34 ml of water-saturated (about 2 wt %) nitrogen-purged methyl-t-butyl ether were introduced cobalt TPP and dicobalt octacarbonyl. The reactor was pressured with 700 psig of 2:1 $H_2/CO$. The reaction solution was then heated with stirring, and 1.5g (34 mmoles) of ethylene oxide was charged to the reaction vessel after the reaction temperature had been reached. The pressure was increased to about 1500 psig with additional $H_2/CO$. Stirring was continued for 1 hour and the reaction mixture was cooled to 5° C. The gases were slowly vented to ambient pressure and 20 ml of nitrogen-purged deionized water were injected. The reaction mixture was stirred for 5 minutes and the phases were then allowed to separate. The water phase containing the reaction product was removed and analyzed by gas chromatography. Results are shown in Table 1.

In some instances, the reactor containing the remaining methyl-t-butyl ether and catalyst was repressured to 700 psig with $H_2/CO$ and heated to reaction temperature. After 30 minutes, 1.5 g of ethylene oxide was again injected and the pressure was increased to about 1500 psig with additional $H_2/CO$. After stirring for 1 hour under reaction conditions, the reaction mixture was cooled, vented to ambient pressure, extracted with deionized water, and phase separated under an inert atmosphere. The aqueous and organic phases were analyzed for product content by gas chromatography. In several instances, the separated phases were also analyzed for metal content. The Experiment using this "recycled" catalyst is designated with an "R" in the Table.

As can be seen from the results, cobalt TPP has a promotional effect for the dicobalt octacarbonyl catalyst. A comparison of Run 1 with Run 3 shows that the cobalt porphyrin, present only in Run 3, increased conversion of ethylene oxide from 29% to 58% at 70° C. The cobalt porphyrin alone (Run 2) did not catalyze ethylene oxide hydroformylation under these conditions; the porphyrine is thus acting as a promoter for cobalt catalysis.

A comparison of Run 1 with Runs 7 and 8 (Table 1) shows that the improved ethylene oxide conversion obtained is due to the metal porphyrin promoter, not to any porphine (amine) complexed to the cobalt metal in the metal porphyrin. The 5,10,15,20-tetraphenyl-21H,23H-porphine added to the reaction solution containing dicobalt octacarbonyl had no effect on ethylene oxide conversion.

Runs 3, 5 and 6 (Table 1) show that the metal porphyrin promoter is effective even at very low concentrations.

EXAMPLE 2

This example illustrates the hydroformylation of propylene oxide catalyzed by a cobalt porphyrin-promoted cobalt catalyst in accordance with the invention process.

A 100-ml Parr autoclave was charged with 115 mg (0.34 mmole) of dicobaltoctacarbonyl, 25 mg (0.037 mmole) of 5,10,15,20-tetraphenyl-21H,23H-porphine cobalt(II), 34 ml of water-saturated (about 2 wt %) nitrogen-purged methyl-t-butyl ether, and 1.98 g propylene oxide (34 mmole). The reaction mixture was heated with stirring at 80° C. and 1400 psig $H_2/CO$ (2:1) for 1 hour and then cooled to 5° C. The gases were slowly vented to ambient pressure, and 25 ml of nitrogen-purged, deionized water were injected into the reactor. After stirring for 5 minutes and allowing phase separation, the water phase was removed from the reactor and analyzed by gas chromatography. Selectivities to the organic products were 19.6% acetone, 64.1% 3-hydroxybutyraldehyde, 11.7% 2-methylpropionaldehyde and 4.6% 1,3-butanediol. Propylene oxide conversion was 70%.

TABLE 1

| | | | | Hydroformylation of Ethylene Oxide (EO) | | | |
|---|---|---|---|---|---|---|---|
| | Catalyst[b] | | Temp. | EO Conversion | Selectivity, (mole %) | | |
| Run[a] | (mmole of metal) | | (°C.) | (%) | AA[c] | 3-HPA[c] | 1,3-PDO[c] |
| 1 | $Co_2(CO)_8$ 0.67 | | 70 | 29 | 6.2 | 93.8 | — |
| 2 | Cobalt TPP | | 70 | 0 | — | — | — |
| 3 | $Co_2(CO)_8$ (0.67) Cobalt TPP (0.037) | | 70 | 58 | 8.1 | 91.9 | — |
| 4R | $Co_2(CO)_8$ (0.67) Cobalt TPP (0.037) | | 70 | 52 | 12.9 | 87.1 | — |
| 5 | $Co_2(CO)_8$ (0.67) Cobalt TPP (0.02) | | 70 | 43 | 13.4 | 86.6 | — |
| 6 | $Co_2(CO)_8$ (0.67) Cobalt TPP (0.01) | | 70 | 36 | 7.4 | 92.6 | — |
| 7 | $Co_2(CO)_8$ (0.67) TPP (0.037) $Co_2(CO)_{12}$ 0.67 | | 70 | 30 | 7.4 | 92.6 | — |
| 8 | $Co_2(CO)_8$ (0.74) TPP (0.037) | | 70 | 30 | 12.3 | 87.7 | — |
| 9 | $Co_2(CO)_8$ (0.67) Cobalt TMeOPP (0.037) | | 70 | 49 | 10.8 | 89.2 | — |
| 10 | $Co_2(CO)_8$ (0.67) Cobalt OEP (0.037) | | 70 | 43 | 9.2 | 90.8 | — |
| 11 | $Co_2(CO)_8$ (0.67) OEP (0.037) | | 70 | 25 | 7.2 | 92.8 | — |

[a]"R" indicates that the methyl-t-butyl ether solution containing the cobalt catalyst and promoter from the run listed immediately above was used for the experiment.
[b]Amounts of cobalt catalyst and metal porphyrin promoter are given in millimoles of the respective metal atoms (not millimoles of compound introduced). $Co_2(CO)_8$ is dicobalt octacarbonyl, cobalt TPP is 5,10,15,20-tetraphenyl-21H,23H-porphine cobalt(II), and TPP is 5,10,15,20-tetraphenyl-21H,23H-porphine, cobalt TMeOPP is meso-tetramethoxyphenyl cobalt (II), cobalt OEP is 2,3,7,8,12,13,17,18-octaethyl-21H,23H-porphine cobalt(II), and OEP is 2,3,7,8,12,13,17,18-octaethyl-21H,23H-porphine.
[c]3-HPA - 3-hydroxypropionaldehye
1,3-PDO = 1,3-propanediol
AA = acetaldehyde

We claim:

1. A process for preparing an alkanediol comprising the steps of:

(a) contacting, at a temperature within the range of about 50° to about 100° C. and a pressure within the range of about 500 to about 5000 psig, an ethylene oxide with carbon monoxide and hydrogen in an essentially non-water miscible solvent in the presence of an effective amount of a non-phosphine-ligated cobalt or rhodium catalyst and an effective amount of a cobalt or rhodium porphyrin promoter under reaction conditions effective to produce an intermediate product mixture comprising less than 15 wt % hydroxyaldehyde;

(b) adding an aqueous liquid to said intermediate product mixture and extracting into said aqueous liquid a major portion of the hydroxyaldehyde at a temperature less than about 100° so as to provide an aqueous phase comprising the hydroxyaldehyde in greater concentration than the concentration of hydroxyaldehyde in the intermediate product mixture, and an organic phase comprising at least a portion of the cobalt or rhodium catalyst and at least a portion of the porphyrin promoter;

(c) separating the aqueous phase from the organic phase;

(d) contacting the aqueous phase comprising the hydroxyaldehyde with hydrogen in the presence of a hydrogenation catalyst at a pressure of at least about 100 psig and a temperature during at least a portion of the hydrogenation step of at least about 40° C. to provide a hydrogenation product mixture comprising an alkanediol; and (e) recovering the alkanediol from the hydrogenation product mixture.

2. The process of claim 1 in which the solvent of step (a) comprises an ether.

3. The process of claim 1 in which the hydroxyaldehyde in the intermediate product mixture is produced at a level within the range of about 5 to about 10 wt %.

4. The process of claim 3 in which step (a) is carried out at a temperature within the range of about 65° to about 80° C.

5. The process of claim 4 in which step (a) is carried out at a pressure within the range of about 1000 to about 3500 psig.

6. The process of claim 1 in which the porphyrin promoter is 5,10,15,20-tetraphenyl-21H,23H-porphine cobalt(II).

7. The process of claim 5 in which the solvent of step (a) has an Ostwald coefficient for carbon monoxide solubility greater than 0.15 v/v.

8. The process of claim 5 in which the solvent of step (a) comprises methyl-t-butyl ether.

9. The process of claim 1 in which water is present in step (a) in an amount within the range of about 1 to about 2.5 wt %.

10. The process of claim 1 in which the alkanediol is 1,3-propanediol and the alkylene oxide is ethylene oxide.

11. The process of claim 1 in which the metal porphyrin promoter is present in step (a) in an amount within the range of about 0.001 to about 0.5 moles per mole of cobalt.

12. The process of claim 1 in which the carbon monoxide and hydrogen of step (a) are present in an $H_2/CO$ ratio within the range of about 1.5:1 to about 5:1.

13. The process of claim 1 in which the metal porphyrin promoter is present in step (a) in an amount within the range of about 0.0008 to about 0.1 mole per mole of cobalt.

14. A process for preparing 1,3-propanediol comprising the steps of:

(a) reacting ethylene oxide, carbon monoxide and hydrogen in a solvent comprising methyl-t-butyl ether at a temperature within the range of about 50 to about 100° C. in the presence of a catalytic amount of a non-phosphine-ligated cobalt carbonyl and a promoting amount of a cobalt porphyrin, under hydroformylation conditions effective to produce an intermediate product mixture comprising less than 15 wt % 3-hydroxypropanal;

(b) adding water to said intermediate product mixture in an amount within the range of about 5 to about 20 weight percent based on the weight of the intermediate product mixture, and permitting the water-containing intermediate product mixture to resolve into an aqueous phase comprising 3-hydroxypropanal in a concentration greater than about 20 wt %, and an organic phase comprising a major portion of the cobalt porphyrin and the cobalt carbonyl;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature of at least about 40° C. to provide a hydrogenation product mixture comprising 1,3-propanediol; and (e) recovering 1,3-propanediol from the hydrogenation product mixture.

15. The process of claim 14 in which the cobalt porphyrin is present in step (a) in an amount within the range of about 0.001 to about 0.5 mole per mole of cobalt in the cobalt catalyst.

16. The process of claim 14 in which the aqueous phase of step (b) comprises 3-hydroxypropanal in a concentration greater than about 20 wt %.

17. The process of claim 14 in which the cobalt porphyrin is present in step (a) in an amount within the range of about 0.008 to about 0.1 mole per mole of cobalt in the cobalt catalyst.

18. The process of claim 14 which further comprises recycling the organic phase of step (c) to the process of step (a).

19. The process of claim 14 in which the cobalt porphyrin is 5,10,15,20-tetraphenyl-21H,23H-porphine cobalt(II).

* * * * *